United States Patent [19]

Wilk et al.

[11] Patent Number: 5,383,883

[45] Date of Patent: Jan. 24, 1995

[54] METHOD FOR ULTRASONICALLY APPLYING A SURGICAL DEVICE

[76] Inventors: Peter J. Wilk, 185 W. End Ave., New York, N.Y. 10023; Mitchell N. Essig, 227 High Brook Ct., Pelham, N.Y. 10803

[21] Appl. No.: 72,762

[22] Filed: Jun. 7, 1992

[51] Int. Cl.⁶ .................................................. A61B 17/00
[52] U.S. Cl. .................................... 606/169; 606/142; 606/213; 604/22
[58] Field of Search ............... 606/1, 142, 143, 213, 606/215, 216, 139, 169; 604/22; 607/97

[56] References Cited

U.S. PATENT DOCUMENTS

| | | | |
|---|---|---|---|
| 3,308,003 | 3/1967 | Deans | 606/169 |
| 3,513,848 | 5/1970 | Winston et al. | 606/228 |
| 3,618,594 | 11/1971 | Banko | 606/169 |
| 3,898,992 | 8/1975 | Balamuth | 606/169 |
| 4,805,618 | 2/1989 | Ueda et al. | 128/831 |
| 4,931,047 | 6/1990 | Broadwin et al. | 606/169 |
| 5,015,227 | 5/1991 | Broadwin et al. | 606/169 |
| 5,171,251 | 12/1992 | Bregen et al. | 606/157 |
| 5,207,691 | 5/1993 | Nardella | 606/143 |
| 5,217,460 | 6/1993 | Knoepfler | 606/205 |

Primary Examiner—Stephen C. Pellegrino
Assistant Examiner—Jeffrey A. Schmidt
Attorney, Agent, or Firm—R. Neil Sudol; Henry D. Coleman

[57] ABSTRACT

In a laparoscopic surgical closure method, a distal end portion of a laparoscopic instrument is inserted into an abdominal cavity of a patient through a trocar sleeve disposed in an abdominal wall of the patient. A surgical device such as a clip or a suture having two portions made of polymeric material is applied to an organic structure inside the patient. The instrument is manipulated to place the bonding component in operative contact with the surgical device upon application of the surgical device to the organic structure. Subsequently, the bonding component is operated to bond the two portions of the surgical device to one another to lock the surgical device to the organic structure. The bonding component at the distal end of the laparoscopic instrument may include a heat exchanger and/or an ultrasonic transducer.

7 Claims, 2 Drawing Sheets

METHOD FOR ULTRASONICALLY APPLYING A SURGICAL DEVICE

BACKGROUND OF THE INVENTION

This invention relates to a surgical technique and an associated instrument assembly. More particularly, this invention relates to a method and an associated instrument for applying a surgical device such as a clip or suture. The method and instrument assembly are particularly useful in laparoscopic surgery.

Laparoscopic surgery involves the insufflation of the abdominal cavity with carbon dioxide and the placement of cannulas in the abdominal wall of the patient. Distal end portions of laparoscopic instruments are inserted through the cannulas for performing an operation inside the abdominal cavity by surgeons manipulating the proximal ends of the instruments. Laparoscopic instruments include a fiber-optic laparoscope which enables visual monitoring of abdominal organs, as well as the distal end portions of the operating instruments.

Performing an operation laparoscopically, instead of via a traditional open incision, provides the substantial benefits of reducing patient trauma and hospital convalescent time. For these reasons, the number of laparoscopic surgical operations has increased enormously in the past few years. In particular, common laparoscopic operations include the removal of gall bladders (cholecystectomies) and various gynecological procedures. In a cholecystectomy, surgical clips or staples are applied to the cystic duct prior to the severing of that duct. Surgical clips or ligating sutures are also applied to the Fallopian tubes.

OBJECTS OF THE INVENTION

An object of the present invention is to provide a method for use in applying a surgical device such as a clip or suture.

Another object of the present invention is to provide such a method which is utilizable in a laparoscopic procedure.

A further object of the present invention is to provide an instrument assembly for assisting in locking a clip or a suture in a laparoscopic porcedure.

These and other objects of the present invention will be apparent from the drawings and detailed descriptions herein.

SUMMARY OF THE INVENTION

A laparoscopic surgical device comprises, in accordance with the present invention, an elongate shaft and a bonding component at a distal end of the shaft for bonding polymeric portions of a surgical device to one another upon an application of the surgical device to a structure inside a patient. An actuator is disposed in part at a proximal end of the shaft and is operatively connected to the bonding component for operating the bonding component to bond the polymeric portions of the surgical device to one another.

According to one of several alternative features of the present invention, the surgical device is a clip and the polymeric portions are legs of the clip. The device then further comprises an applicator at a distal end of the shaft for applying the clip to the structure inside the patient. The clip is seated in the applicator which may take the forms of a pair of forceps jaws.

The surgical device may be a combination of a locking element and a tack, the locking element being fastened to the tack by the bonding component of the device. Alternatively, the surgical device may be a polymeric suture.

According to another feature of the present invention, the bonding component includes a heat exchanger for increasing the temperature of the polymeric portions of the surgical device above a predetermined threshold. Alternatively or additionally, the bonding component includes an ultrasonic wave generator for generating an ultrasonic signal and transmitting the signal to the surgical device.

The structure to which the surgical device is applied may be an internal organic structure of the patient, such as a Fallopian tube or a cystic duct. The structure may be another surgical device such as a tack or a suture to which the surgical device (e.g., a clip) is secured.

A method for use in operating on a patient, in accordance with the present invention, utilizes a laparoscopic trocar sleeve and a laparoscopic instrument comprising an elongate shaft and bonding component provided at a distal end of the shaft for bonding polymeric materials. The method comprises the steps of (i) disposing the trocar sleeve in an abdominal wall of a patient, (ii) inserting a distal end portion of the laparoscopic instrument through the sleeve and into an abdominal cavity of the patient, (iii) applying a surgical device having two portions made of polymeric material to an organic structure inside the patient, (iv) manipulating the instrument to place the bonding component in operative contact with the surgical device upon application thereof to the organic structure, and (v) operating the bonding component to bond the two portions of the surgical device to one another to lock the surgical device to the organic structure.

Where the two portions of the surgical device include a tack and a locking element at one end of the tack, the surgical device is applied to the organic structure by passing the tack through the structure and subsequently positioning the locking element at the one end of the tack. This procedure may be accomplished laparoscopically by positioning an additional laparoscopic trocar sleeve in the abdominal wall of the patient, inserting a distal end portion of a tack ejecting instrument into the abdominal cavity of the patient through the additional trocar sleeve and operating the tack ejecting instrument to push the tack through the organic structure.

Where the surgical device is a clip and the two portions of the surgical device are two legs of the clip, the instrument may further include an applicator at a distal end of the shaft for holding the surgical clip and applying the surgical clip to a structure inside a patient.

Where the surgical device is a suture and the two portions of the surgical device are end portions of the suture, the surgical device is applied by twisting the end portions of the suture about one another.

According to a specific feature of the present invention, an ultrasonic signal is generated and transmitted to the surgical device to bond the two portions of the surgical device to one another upon application of the surgical device to the organic structure. Alternatively or additionally, heat energy is generated and conveyed to the surgical device upon application of the surgical device to the structure.

In accordance with a more general conceptualization of the present invention, a method for use in operating on a patient comprises the steps of providing a surgical device with two portions made of a polymeric material, applying the surgical device to a structure in a patient, and bonding the two portions of the surgical device to one another upon application of the surgical device to the structure to form a continuous weld between the two portions.

The bonding may be accomplished ultrasonically and/or thermally. The bonding may be performed in a laparoscopic operation.

DETAILED DESCRIPTION

Figure 1:
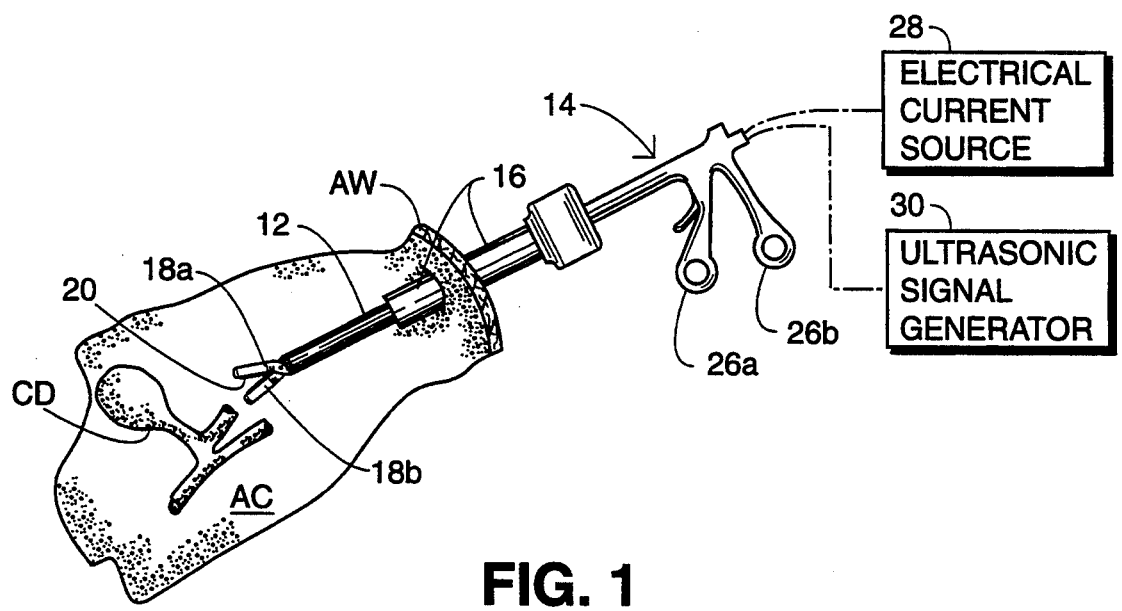
FIG. 1 is partially a block diagram and partially a schematic side elevational view of a laparoscopic instrument or device inserted through an abdominal wall of a patient for performing a clipping operation in accordance with the present invention.

As illustrated in FIG. 1, a distal end portion 12 of a laparoscopic instrument of device 14 is inserted into an abdominal cavity AC of a patient through a trocar sleeve 16 disposed in an abdominal wall AW of the patient. At a distal end, instrument 14 is provided with a pair of forceps jaws 18a and 18b. A surgical clip 20 made of a biologically compatible polymeric material is seated between jaws 18a and 18b. Clip 20 (FIG. 2) has a pair of legs 22a and 22b joined at their proximal ends by a bight 24.

Instrument 14 is manipulated from outside the patient to place forceps jaws 18a and 18b about an internal organ of the patient, such as a cystic duct CD or other tubular member. A pair of actuator handles 26a and 26b are then operated to close forceps jaws 18a and 18b and thereby close clip 20 about cystic duct CD.

Figure 2:
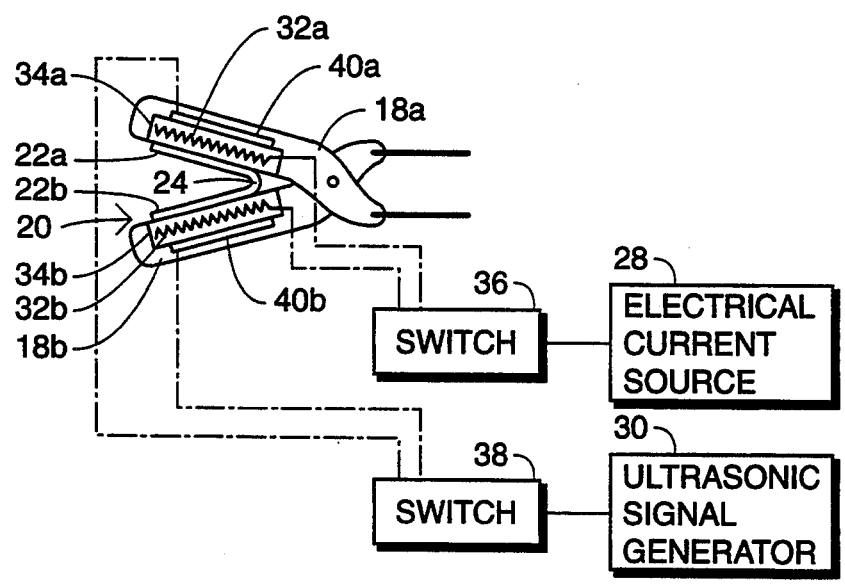
FIG. 2 is partially a block diagram of the device of FIG. 1 and partially a schematic side elevational view of a distal end portion of the device.

As illustrated in FIGS. 1 and 2, instrument 14 is operatively connected to an electrical current source 28 and/or to an ultrasonic signal generator 30. More specifically, current source 28 is coupled to a pair of resistors 32a and 32b mounted to forceps jaws 18a and 18b, respectively. Resistors 32a and 32b are in turn in heat conductive contact with respective metallic plates 34a and 34b disposed along inner faces (not designated) of jaws 18a and 18b. Plates 34a and 34b serve as heat exchangers which bring clip 20 to a predetermined temperature upon closure of a switch 36 connecting current source 28 to resistors 32a and 32b. Legs 22a and 22b are made, for example, of a polymeric thermosetting material which can reform and thereby weld legs 22a and 22b to one another upon the application of sufficiently high temperature and pressure.

The bonding of legs 22a and 22b to one another via a weld is facilitated by the transmission of an ultrasonic pressure wave to legs 22a and 22b. A switch 38 (FIG. 2) connects signal generator 30 to one or two crystalline piezoelectric transducers 40a and 40b in operative mechanical contact with plates 34a and 34b. The ultrasonic vibration produced by crystalline transducers 40a and 40b is conducted through plates 34a and 34b to clip 20. In some cases, the ultrasonic vibration may be sufficient to reform the polymeric material of legs 22a and 22b and thereby weld the legs to one another.

Upon the application of clip 20 by forceps jaws to cystic duct CD, switch 36 and/or switch 38 is operated to bond legs 22a and 22b to one another and lock clip 20 to duct CD.

Figure 3:
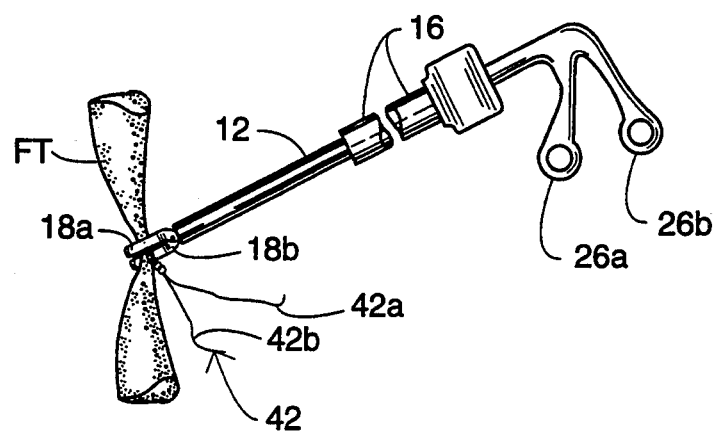
FIG. 3 is a partial schematic side elevational view of the laparoscopic instrument or device of FIGS. 1 and 2 used in welding a suture in a procedure in accordance with the present invention.

As depicted in FIG. 3, instrument 14 may be used to weld end portions 42a and 42b of a suture 42 to one another upon application of the suture, for example, to a tubular organic structure such as a Fallopian tube FT to ligate the tube. In this case, clip 20 may be omitted.

Upon a disposition of suture 42 about Fallopian tube FT and a twisting of suture end portions 42a and 42b about one another, instrument 14 is manipulated from outside the patient to place forceps jaws 18a and 18b about the twisted end portions 42a and 42b. Actuator handles 26a and 26b are then operated to close forceps jaws 18a and 18b and thereby place plates 34a and 34b in heat and vibration conductive contact with suture ends 42a and 42b. Switch 36 and/or switch 38 is operated to thermally and/or ultrasonically bond suture end portions 42a and 42b to one another and lock suture 42 to tube FT.

Figure 4:
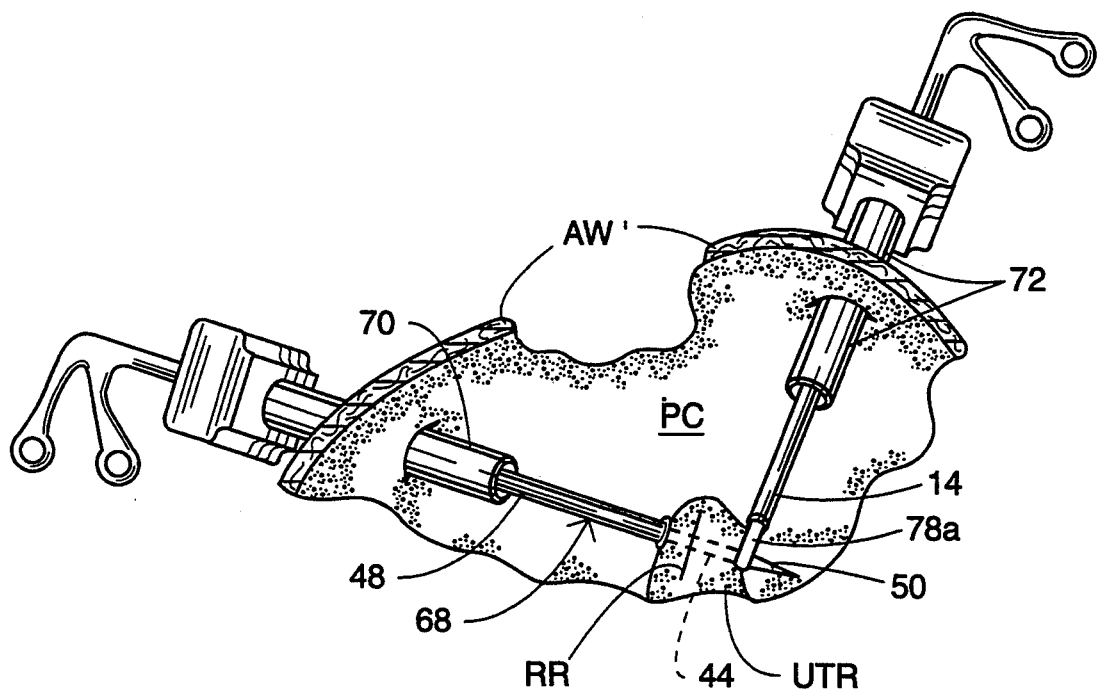
FIG. 4 is a schematic perspective view, partially broken away and partially in cross-section, of the laparoscopic device of FIGS. 1-3 being used to attach a locking clip to a free end of a tack in a laparoscopic operation, in accordance with the present invention.

As depicted in FIG. 4, a surgical tack 44 is ejected through uterine tissues UTR to effectuate closure of a ressected region RR of a uterus UTR. A distal end portion 48 of an elongate tack ejector 68 is inserted into the abdominal or peritoneal cavity PC of a patient via a first laparoscopic trocar sleeve 70. Sleeve 70, as well as a second trocar sleeve 72, traverses an abdominal wall AW' of the patient. Instrument 14 is inserted through sleeve 72 and applies clip 20 (FIGS. 1 and 2) to a distal end portion 50 of tack 44. In this case, the bonding or welding may be effectuated between clip 20 and tack 44, as well as between legs 22a and 22b of clip 20.

Although the invention has been described in terms of particular embodiments and applications, one of ordinary skill in the art, in light of this teaching, can generate additional embodiments and modifications without departing from the spirit of or exceeding the scope of the claimed invention. For example, it is to be noted that the locking of clips and/or sutures during conventional open-incision surgery may also be effectuated via the application of heat and/or ultrasonic mechanicam vibration as described in detail hereinabove with respect to laparoscopic surgery.

Accordingly, it is to be understood that the drawings and descriptions herein are proffered by way of example to facilitate comprehension of the invention and should not be construed to limit the scope thereof.

What is claimed is:

1. A method for use in operating on a patient, comprising the steps of:
    Providing a surgical device with two portions made of a polymeric material;
    applying said surgical device to a structure in a patient; and
    upon application of said surgical device to the structure, bonding said two portions to one another to form a continuous weld between said two portions, said step of bonding including the steps of generating an ultrasonic signal and transmitting said signal into said two portions upon application of said surgical device to the structure;

wherein said steps of applying and bonding are performed by inserting a laparoscopic instrument into a patient through a laparoscopic trocar sleeve.

2. A method for use in operating on a patient, comprising the steps of:
providing a laparoscopic trocar sleeve and a laparoscopic instrument comprising an elongate shaft and bonding means provided at a distal end of said shaft for bonding polymeric materials;
disposing said trocar sleeve in an abdominal wall of a patient;
inserting a distal end portion of said laparoscopic instrument through said sleeve and into an abdominal cavity the patient;
applying a surgical device to an organic structure inside the patient, said surgical device having two portions made of polymeric material, said surgical device being a suture said two portions are end portions of said suture, said step of applying including the step of twisting said end portions about one another;
manipulating said instrument to place said bonding means in operative contact with said surgical device upon cation thereof to the organic structure; and
operating said bonding means to bond said two portions of said surgical device to one another to lock said surgical device to the organic structure.

3. A method for use in operating on a patient, comprising the steps of:
providing a laparoscopic trocar sleeve and a laparoscopic instrument comprising an elongate shaft and bonding means provided at a distal end of said shaft for bonding polymeric materials;
disposing said trocar sleeve in an abdominal wall of a patient;
inserting a distal end portion of said laparoscopic instrument through said sleeve and into an abdominal cavity of the patient;
applying a surgical device to an organic structure inside the patient, said surgical device having two portions made of polymeric material, said two portions of said surgical device including a tack and a locking element at one end of the tack, said step of applying including the steps of passing said tack through the organic structure inside the patient and subsequently positioning said locking element at said one end of said tack;
manipulating said instrument to place said bonding means in operative contact with said surgical device upon application thereof to the organic structure; and
operating said bonding means to bond said two portions of said surgical device to one another to lock said surgical device to the organic structure.

4. The method defined in claim 3 wherein said step of operating includes the steps of generating an ultrasonic signal and transmitting said signal to said surgical device upon application of said surgical device to the organic structure.

5. The method defined in claim 3 wherein said step of passing includes the steps of:
positioning an additional laparoscopic trocar sleeve in the abdominal wall of the patient;
inserting a distal end portion of a tack ejecting instrument into the abdominal cavity of the patient through said additional trocar sleeve; and
operating said tack ejecting instrument to push said tack through the organic structure.

6. The method defined in claim 3 wherein said step of operating includes the steps of generating an ultrasonic signal and transmitting said signal to said surgical device upon application of said surgical device to said organic structure.

7. The method defined in claim 3 wherein said step of operating includes the steps of generating heat energy and conveying said heat energy to said surgical device upon application of said surgical device to the structure during said step of operating.

* * * * *

UNITED STATES PATENT AND TRADEMARK OFFICE
CERTIFICATE OF CORRECTION

PATENT NO. : 5,383,883
DATED : January 24, 1995
INVENTOR(S) : Peter J. Wilk and Mitchell N. Essig It is certified that error appears in the above-indentified patent and that said Letters Patent is hereby corrected as shown below:

Column 5, line 15 (claim 2), insert --of-- after "cavity", line 25 (claim 2), replace "cation" with --application--.

Signed and Sealed this

Eighteenth Day of April, 1995

Attest:

BRUCE LEHMAN

*Attesting Officer*

*Commissioner of Patents and Trademarks*